(12) United States Patent
Wang et al.

(10) Patent No.: US 6,793,788 B2
(45) Date of Patent: Sep. 21, 2004

(54) METHOD AND DEVICE FOR HYDROGEN AND HYDROCARBON SENSING

(75) Inventors: Da Yu Wang, Troy, MI (US); Kaius K. Polikarpus, Grand Blanc, MI (US); Walter T. Symons, Grand Blanc, MI (US); Frederick L. Kennard III, Holly, MI (US); Ming-Cheng Wu, Rochester Hills, MI (US)

(73) Assignee: Delphi Technologies, Inc., Troy, MI (US)

(*) Notice: Subject to any disclaimer, the term of this patent is extended or adjusted under 35 U.S.C. 154(b) by 56 days.

(21) Appl. No.: 10/117,566

(22) Filed: Apr. 5, 2002

(65) Prior Publication Data

US 2002/0139691 A1 Oct. 3, 2002

Related U.S. Application Data

(63) Continuation-in-part of application No. 09/684,415, filed on Oct. 6, 2000.

(51) Int. Cl.$^7$ .................. G01N 27/407; B05D 5/12
(52) U.S. Cl. ................ 204/424; 204/429; 427/125; 264/618
(58) Field of Search ................. 204/421–429; 427/125, 126.5; 264/614, 618

(56) References Cited

U.S. PATENT DOCUMENTS

| | | | |
|---|---|---|---|
| 3,843,400 A | * | 10/1974 | Radford et al. |
| 3,904,703 A | * | 9/1975 | Lo et al. .................. 585/441 |
| 4,021,326 A | * | 5/1977 | Pollner et al. |
| 4,476,008 A | * | 10/1984 | Sano et al. |
| 4,487,680 A | * | 12/1984 | Logothetis et al. |
| 4,514,277 A | * | 4/1985 | Sakurai et al. ............ 204/424 |
| 4,547,281 A | | 10/1985 | Wang et al. ............... 204/424 |
| 4,582,657 A | | 4/1986 | Shibata et al. ............ 264/40.6 |
| 5,122,487 A | * | 6/1992 | Hayakawa et al. |
| 5,395,506 A | | 3/1995 | Duce et al. ............... 204/426 |
| 5,472,580 A | * | 12/1995 | Kennard et al. .......... 205/784.5 |
| 5,670,115 A | | 9/1997 | Cheng et al. .............. 422/90 |
| 5,672,811 A | * | 9/1997 | Kato et al. |
| 5,795,545 A | | 8/1998 | Koripella et al. .......... 422/94 |
| 5,886,614 A | | 3/1999 | Cheng et al. .............. 338/34 |
| 6,051,123 A | * | 4/2000 | Joshi et al. ............... 204/424 |
| 6,227,033 B1 | | 5/2001 | Kainz |
| 6,382,198 B1 | | 5/2002 | Smith et al. |
| 6,453,726 B1 | | 9/2002 | Gutierrez et al. |
| 6,484,561 B2 | | 11/2002 | Jackson et al. |
| 6,514,397 B2 | | 2/2003 | LaBarge et al. |
| 6,544,467 B2 | | 4/2003 | Symons et al. |
| 6,562,747 B2 | | 5/2003 | Symons et al. |
| 6,579,435 B2 | | 6/2003 | Wang et al. |
| 6,579,436 B2 | | 6/2003 | Wang et al. |
| 6,585,872 B2 | | 7/2003 | Donelon et al. |

OTHER PUBLICATIONS

Geyu Lu, Norio Miura, Noboru Yamazoe, "High–temperature hydrogen sensor based on stabilized zirconia and a metal oxide electrode", Sensors and Actuators B 35–36 (1996) 130–135.

David M. Haaland, "Noncatalytic Electrodes for Solid–Electrolyte Oxygen Sensors", J. Electrochem. Soc.: Electrochemical Science and Technology, vol. 127, No. 4, Apr. 1980, pp. 796–803.

S. Thiemann, R. Hartung, H. Wulff, J. Klimke, H.-H. Mobius, U. Guth, U. Schonauer, "Modified Au/YSZ electrodes—preparation, characterization and electrode behaviour at higher temperatures", Solid State Ionics 86–88 (1996) 873–876.

* cited by examiner

*Primary Examiner*—Kaj K. Olsen
(74) *Attorney, Agent, or Firm*—Jimmy L. Funke

(57) ABSTRACT

One embodiment of a method of fabricating a sensor element for an exhaust gas sensing device, comprises disposing an electrolyte in ionic communication with a sensing electrode and a reference electrode to form the sensor element. The sensing electrode comprises an activator comprising silica and an oxide of an element. The element is selected from the group consisting of alkaline earth elements, rare earth elements, and combinations comprising at least one of the foregoing elements.

9 Claims, 1 Drawing Sheet

METHOD AND DEVICE FOR HYDROGEN AND HYDROCARBON SENSING

CROSS REFERENCE TO RELATED APPLICATION

The present application is a continuation-in-part application of U.S. patent application Ser. No. 09/684,415, filed Oct. 6, 2000, which is hereby incorporated by reference in its entirety.

BACKGROUND OF THE INVENTION

The present invention generally relates to methods and devices for sensing components in a gaseous mixture. Particularly this invention relates to improved methods and devices for sensing hydrogen/hydrocarbons using the electrochemical mixed potential effect.

The automotive industry long has sought to monitor exhaust gases issuing from an internal combustion engine, using sensors to detect and analyze such exhaust gas components as hydrogen ($H_2$), oxygen ($O_2$), hydrocarbons (HC), nitrous oxides ($NO_x$), and the like. Being able to monitor the content of the exhaust gas accommodates numerous beneficial results. For example, such information can be applied to the determination of catalytic converter efficiency, the reduction of emissions to meet state and federal requirements, and the adjustment and optimization of air/fuel ratio for combustion in the engine cylinders.

Using the principles of electrochemistry, one can employ a mixed potential method for sensing hydrogen or hydrocarbons in a gas stream. The principle involved can be expressed by the equation:

$$E = n\left(\frac{kT}{q}\right)\log(P_{HC}) - m\left(\frac{kT}{q}\right)\log(P_{O_2}) + \left(\frac{kT}{q}\right)\log\left(\frac{K_{HC}}{K_{O_2}}\right)$$

where:
 E=Emf, electromotive force
 n, m, q=constants
 k=Boltzman constant
 T=absolute temperature of the gas in °Kelvin
 $P_{HC}$=partial pressure of $H_2$/HC
 $P_{O_2}$=partial pressure of $O_2$
 $K_{HC}$=exchange charge reaction constant of the sensor system to $H_2$/HC
 $K_{O_2}$=exchange charge reaction constant of the sensor system to $O_2$ As can be observed from this equation, in order to utilize this principle, the electrode/electrolyte system must satisfy the following conditions:
1. none or very little catalytic reaction may occur between hydrogen/hydrocarbon and oxygen at the sensing electrode;
2. the exchange charge reaction rate of oxygen must be less than the exchange charge reaction rate of hydrogen/hydrocarbon; and
3. there must be constant exchange charge rate constants with respect to time and ambient environment.

There have been found numerous materials that exhibit the requisite lack of catalytic reaction to satisfy the first listed condition. Such electrode materials include Pt, Au, Au/Pt alloys, Pd, Pd/Pt alloys, Ag, Ag/Pt alloys, ZnO, CdO, and the like. However, these materials also feature exchange charge rates that limit their utility pursuant to conditions 2 and 3, above. In addition, such materials have serious aging effects and usually exhibit instability towards the ambient atmosphere. A sensing electrode continues to be needed which can satisfy all of the required conditions.

SUMMARY OF THE INVENTION

Disclosed herein are sensor elements, methods for fabricating sensor elements, and methods for sensing a gas. One embodiment of a method of fabricating a sensor element for an exhaust gas sensing device, comprises disposing an electrolyte in ionic communication with a sensing electrode and a reference electrode to form the sensor element. The sensing electrode comprises an activator comprising silica and an oxide of an element. The element is selected from the group consisting of alkaline earth elements, rare earth elements, and combinations comprising at least one of the foregoing elements.

One embodiment of the sensor element comprises an electrolyte in ionic communication with a sensing electrode and a reference electrode. The sensing electrode comprises an activator comprises silica and an oxide of an element. The element is selected from the group consisting of alkaline earth elements, rare earth elements, and combinations comprising at least one of the foregoing elements.

One embodiment of the method for sensing a gas comprises: exposing a sensing electrode and a reference electrode to the gas and detecting hydrogen in the gas.

The above described and other features are exemplified by the following figures and detailed description.

BRIEF DESCRIPTION OF THE DRAWINGS

Referring now to the figure, which are meant to be exemplary, not limiting.

DETAILED DESCRIPTION OF THE PREFERRED EMBODIMENT

Figure 1:
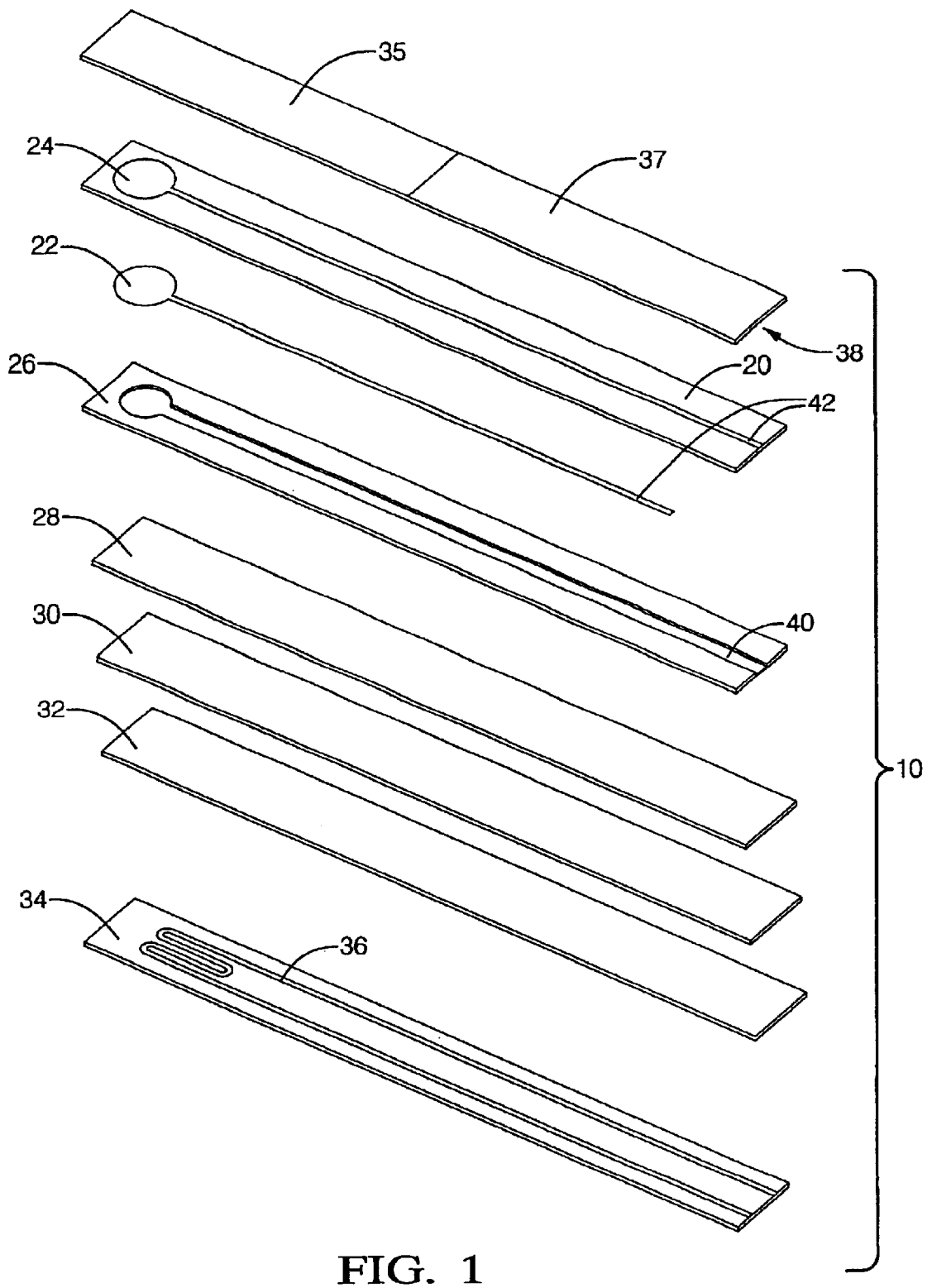
FIG. 1 is an exploded view of one embodiment of a planar exhaust sensor element.

A flat plate, planar automotive exhaust sensor operates in a manner analogous to conical-shaped exhaust sensors. Planar exhaust elements, comprising a plurality of annealed, rectangular layers are known to reach operating temperatures more rapidly than conical sensors. In a planar sensor, a first porous catalytic sensing electrode is exposed to the exhaust gases from an internal combustion engine, while a second porous catalytic reference electrode, disposed opposite an electrolyte substrate from the sensing electrode, is exposed to a reference gas (see FIG. 1). The resulting galvanic potential between the two electrodes then is measured and is indicative of the exhaust gas composition. The difference between the conical-shaped sensor and the planar sensor is that the planar sensor, i.e., the electrolyte layer, the sensing and reference electrodes, and an optional heater element, all are provided as flat components to form a layered planar structure.

A sensing element for an exhaust gas sensor comprises an electrolyte that is bound by at least two electrodes. The first, sensing electrode is exposed to a sensing atmosphere such as an exhaust gas. The second, reference electrode is exposed to a reference gas. Usually, one or more heaters are attached to the device to maintain the device at a sufficient temperature for performing a sensing operation. The emf measured between the two electrodes, due to galvanic potential, represents the activity difference between the sensing exhaust atmosphere and the reference gas. This activity difference can be interpreted to be indicative of the content of a selected gas component in the exhaust gas stream.

The electrolyte, which is porous or solid and which can comprise the entire layer or a portion thereof, can be any material that is compatible with the environment in which sensor element will be utilized (e.g., up to about 1,000° C.). Possible electrolyte materials can comprise any material employed as sensor electrolytes, including metal oxides such as zirconia, ceria and rare-earth pyrochlore compound (such as $Gd_2Ti_2O_7$), and the like, which are usually doped with calcium (Ca), barium (Ba), yttrium (Y), lanthanum (La), cesium (Cs), magnesium (Mg), aluminum (Al), gadolinium (Gd), and the like, as well as oxides and combinations comprising at least one of the foregoing electrolyte materials. For example, the electrolyte can be alumina and/or yttrium stabilized zirconia. Typically; the electrolyte has a thickness of up to about 500 microns, with a thickness of approximately 25 microns to about 500 microns preferred, and a thickness of about 50 microns to about 150 microns especially preferred.

The electrodes are disposed on the same or opposite sides of the electrolyte and in ionic communication therewith. The electrodes can comprise various metals, such as palladium (Pd), zirconium (Zr), yttrium (Y), cerium (Ce), calcium (Ca), aluminum (Al), gold (Au), platinum (Pt), osmium (Os), rhodium (Rh), iridium (Ir), ruthenium (Ru), nickel (Ni), copper (Cu), tin (Sn), and the like, as well as alloys, oxides, and combinations comprising at least one of the foregoing metals. The sensing electrode and the reference electrode may comprise the same, or a different electrode metal. A preferred metal for the reference electrode is Pt; a preferred material for the sensing electrode is a Au/Pt alloy. The electrodes may be fabricated in any manner, such as sputtering, chemical vapor deposition, screen printing, painting, spraying, dipping, and stenciling, among others, with screen printing electrodes on opposite sides of the electrolyte or layers adjacent thereto preferred due to simplicity, economy, and compatibility with the subsequent co-fired process. Screen printing an ink is further preferred for producing the sensing electrode for the simplicity of incorporating the activator.

An activator is introduced into the sensor element system, by incorporating select activators into the sensing electrode during fabrication thereof. Incorporation of the activator into the sensing electrode and not into the reference electrode enables the electrodes to be exposed to the same gas stream and to detect the hydrogen concentration thereof. The activators comprise silica ($SiO_2$) and oxides of an element including alkaline earth element(s), a rare earth element(s), and combinations comprising at least one of the foregoing elements. Preferred alkaline earth elements include Ba, Sr (strontium), and Ca, and combinations comprising at least one of the foregoing elements; preferred rare earth elements are hafnium (Hf), zirconium (Zr), bismuth (Bi), scandium (Sc), Y, La, Gd, and ytterbium (Yb), and combinations comprising at least one of the foregoing elements.

The activator can be present in amounts less than or equal to about 5 weight percent (wt %), based upon the total solid content of the ink, balance electrode materials (e.g., metals, oxides, alloys, and combinations thereof as described above), with about 0.5 wt % to about 5 wt % activator preferred. The composition of the activator is preferably about 10 wt % to about 40 wt % silica ($SiO_2$) and about 60 wt % to about 90 wt % alkaline earth element(s) and/or a rare earth element(s), based upon the total weight of the activator. Consequently, the resultant sensing electrode comprises about 0.5 wt % to about 5 wt % activator, base upon the total weight of the sensing electrode.

The preferred formulation of the activators depends on various parameters such as the actual processing steps to be used in fabricating the sensor element, as well as the specific intended application for the gas sensing device to be fabricated. Typical parameters that can influence the formulation include sintering temperature for the sensor assembly, the ambient atmosphere for the sintering operation, the ambient atmosphere in which the sensing device will be employed, the particular dry or wet chemical treatment to be applied to the sensor element after sintering, as well as the types of electrical treatment that the sensor element may be subjected to after sintering.

This ink then is applied to the desired surface of the solid electrolyte via a technique such as screen printing, painting, spraying, or the like. The electrode typically may be formed to be rounded or polygonal shape (e.g., square, rectangular, needle-shaped, round, elliptical, or the like).

Disposed over the electrolyte, on the same side as the sensing electrode, is preferably a protective layer. The protective layer typically comprises a dielectric material such as alumina, and is disposed in physical contact with and covers the sensing electrode. It generally is provided to offer protection to both the sensing electrode the associated electrical leads. This protective layer can be constructed as a composite including high density portion (e.g., substantially impervious to the gas) and an open porosity portion that allows the exhaust gas to be sufficiently sampled.

After assembly of the sensor element, the layered structure then can be sintered at sufficient temperatures to remove volatiles and fugitives and to form a monolithic element. Typically, in a sintering operation, conditions including temperatures of about 1,400° C. to about 1,550° C., in an air atmosphere, for up to about 2 hours or more, are employed.

Referring to the drawings, FIG. 1 shows a sensor element fabricated using thick film technology. FIG. 1 is an exploded view of a sensor element 10 that comprises an electrolyte layer 20, typically zirconia oxide partially stabilized with yttria, with reference electrode 22 and sensing electrode 24 disposed on opposite sides of solid electrolyte 20. Reference electrode 22 and sensing electrode 24 typically are fabricated from platinum or platinum-gold alloys, using standard application techniques such as screen printing. Leads 42 are in electrical communication with each of electrodes 22 and 24. The sensor element 10 further comprises internal support and insulation layers 26, 28, 30, 32, and 34 that are disposed against electrolyte layer 20. A heater element 36 is disposed between insulation layers 32 and 34. Protective layer 38, typically made from a dielectric material such as alumina, is disposed in physical contact with and covers sensing electrode 24 and is provided to offer protection to both the sensing electrode 24 and the sensing electrode lead 42. This protective layer 38 can be constructed as a composite including high density portion 37 and open porosity portion 35 so that the exhaust gas may be sufficiently sampled. The protective layer thus is able to offer poison resistance protection to the sensing electrode 24, as well as handling protection for the sensing electrode lead 42.

Insulation layers 26, 28, 30, and 32 serve to electrically isolate the heater 36 from the sensing and reference electrodes. Protective layer 38 and insulation layer 34 physically cover the sensing electrode 24 and heater element 36, respectively, to provide physical protection against, for example, abrasion, and to isolate electrically these components from external packaging. Typically, the insulating layers are fabricated from dielectric materials, such as alumina.

Although the porosity of the reference electrode 22 typically is sufficient to hold an adequate quantity of gas to act as a reference, a channel 40 for introducing testing gas (in this case the channel 40 has the side way open to the exhaust gas), or air (in this case, the channel 40 has the open as shown in FIG. 1) the reference electrode can be provided as shown between insulation layer 26 and reference electrode 22. This channel 40 readily can be formed, for example, by screen printing the channel pattern below reference electrode 22, using a fugitive ink, and then burning the ink off during the sintering process cycle to form channel 40.

Heater element 36 can be any heater capable of maintaining the sensor element at a sufficient temperature to facilitate the various electrochemical reactions therein. The heater element 36, which is in thermal communication with the sensing electrode, maybe fabricated from platinum, platinum-alumina, palladium, platinum-palladium, and the like, as well as alloys and combinations comprising at least one of the foregoing metals and alloys. In general, such heater elements maybe screen printed onto a substrate, using standard techniques.

During use, regardless of where the reference electrode is located (i.e., on the same or opposite side of the electrolyte as the sensing electrode), both the reference electrode and the sensing electrode are exposed to the gas to be sensed. Due to the use of the activator(s) in the sensing electrode, the sensor is capable of sensing hydrogen in the gas stream. In contrast, electrodes that comprise the same composition (e.g., both of the electrodes comprise activators, or no activators), the sensor is not capable of sensing the hydrogen and both of the electrodes can not be exposed to the gas to be sensed.

Advantages of the current sensor design include elimination of the need for a reference gas since both electrodes can be exposed to the same gas and can even be disposed on the same side of the electrolyte, elimination of the need to correct signal differences caused by changes of background oxygen concentration, and easier packaging due to elimination of the need for a reference gas in combination with the simplicity enabled by allowing both electrodes access to the gas to be sensed.

While preferred embodiments have been shown and described, various modifications and substitutions may be made thereto without departing from the spirit and scope of the invention, including the use of the components taught herein in other conventional sensors. Accordingly, it is to be understood that the apparatus and method have been described by way of illustration only, and such illustrations and embodiments as have been disclosed herein are not to be construed as limiting to the claims.

We claim:

1. A method of fabricating a sensor element for an exhaust gas sensing device, said sensor comprising a sensing electrode and a reference electrode in ionic communication with an electrolyte, said method comprising:

disposing a sensing electrode ink in ionic communication with the electrolyte, wherein the sensing electrode ink comprises an activator comprising silica and an oxide of an element and the element is selected from the group consisting of alkaline earth elements, rare earth elements, and combinations comprising at least one of the foregoing elements, and wherein the activator is not incorporated into the reference electrode, and wherein the sensing electrode ink comprises about 0.5 wt % to about 5 wt % of the activator, based upon a total solid content of the ink, and wherein the activator is composed of about 10 wt % to about 40 wt % of the silica and about 60 wt % to about 90 wt % of the element oxide, based upon the total weight of the activator.

2. The method of claim 1, wherein the element is selected from the group consisting of Ba, Sr, Ca, Hf, Zr, Bi, Sc, Y, La, Gd, Yb, and combinations comprising at least one of the foregoing elements.

3. The method of claim 1, wherein the reference electrode and the sensing electrode are disposed on a first side of the electrolyte.

4. The method of claim 1, further comprising disposing a protective layer on a side of the sensing electrode opposite the electrolyte, and heating the sensor element to a temperature of about 1,400° C. to about 1,550° C.

5. The method of claim 1, wherein the sensing electrode further comprises a platinum-gold alloy.

6. A sensor element, comprising:

an electrolyte in ionic communication with a sensing electrode and a reference electrode, wherein the sensing electrode comprises an activator comprising silica and an oxide of an element wherein the element is selected from the group consisting of alkaline earth elements, rare earth elements, and combinations comprising at least one of the foregoing elements, and wherein the activator is not incorporated into the reference electrode wherein the sensing electrode comprises about 0.5 wt % to about 5 wt % of the activator, based upon the total weight of the sensing electrode, and wherein the activator comprises about 10 wt % to about 40 wt % of the silica and about 60 wt % to about 90 wt % of the element oxide, based upon the total weight of the activator.

7. The sensor element of claim 6, wherein the reference electrode and the sensing electrode are disposed on a first side of the electrolyte.

8. The sensor element of claim 6, wherein the electrolyte is porous.

9. A sensor element, comprising:

an electrolyte in ionic communication with a sensing electrode and a reference electrode, wherein the sensing electrode comprises an activator comprising silica and an oxide of an element wherein the element is selected from the group consisting of alkaline earth elements, rare earth elements, and combinations comprising at least one of the foregoing elements, and wherein the activator is not incorporated into the reference electrode, wherein the sensing electrode comprises about 0.5 wt % to about 5 wt % of the activator, based upon the total weight of the sensing electrode, and wherein the activator comprises about 10 wt % to about 40 wt % of the silica and about 60 wt % to about 90 wt % of the element oxide, based upon the total weight of the activator;

a protective layer disposed on a side of the sensing electrode opposite the electrolyte; and a heater element in thermal communication with the sensing electrode, wherein the heater element is disposed on a side of the electrolyte opposite the sensing electrode.

* * * * *